(12) United States Patent
Nagano et al.

(10) Patent No.: US 6,525,088 B1
(45) Date of Patent: Feb. 25, 2003

(54) AGENT FOR MEASUREMENT OF SINGLET OXYGEN

(75) Inventors: Tetsuo Nagano, 1-28-15, Amanuma, Suginami-ku, Tokyo 167-0032 (JP); Naoki Umezawa, Tokyo (JP)

(73) Assignee: Tetsuo Nagano, Tokyo (JP)

( * ) Notice: Subject to any disclaimer, the term of this patent is extended or adjusted under 35 U.S.C. 154(b) by 0 days.

(21) Appl. No.: 09/623,515
(22) PCT Filed: Mar. 31, 1999
(86) PCT No.: PCT/JP99/01658
§ 371 (c)(1), (2), (4) Date: Jan. 3, 2001
(87) PCT Pub. No.: WO99/51586
PCT Pub. Date: Oct. 14, 1999

(30) Foreign Application Priority Data

Mar. 31, 1998 (JP) ............................................. 10-086086

(51) Int. Cl.⁷ .................. A61K 31/357; C07D 307/94; C07D 311/96; C07D 407/02; C07D 493/10
(52) U.S. Cl. .................. 514/452; 514/454; 514/456; 549/265; 549/360; 549/391; 436/800
(58) Field of Search .................. 514/452, 456, 514/454; 549/265, 360, 391; 436/800

(56) References Cited

U.S. PATENT DOCUMENTS 5,242,835 A 9/1993 Jensen

FOREIGN PATENT DOCUMENTS

JP 3-500817 2/1991

OTHER PUBLICATIONS

T.W. Greene, "Protective Groups in Organic Synthesis, 3rd Edition", John Wiley & Sons, Inc., pp. V–XXI and 368–405, 1999.
Nagano et al., Free Radicals in Clinical Medicine, vol. 7, pp. 35–41, 1993.
Schmitz et al., Tetrahedron, vol. 38, No. 10, pp. 1425–1430, 1982.
Aubry et al., Tetrahedron, vol. 39, No. 4, pp. 623–627, 1983.
Butler et al., Can. J. Chem., vol. 53, pp. 256–262, 1975.
Saito et al., J. Am. Chem. Soc., 107, pp. 6329–6334, 1985.

Primary Examiner—T. A Solola
(74) Attorney, Agent, or Firm—Greenblum & Bernstein, P.L.C.

(57) ABSTRACT

Compounds represented by the following general formula (I):

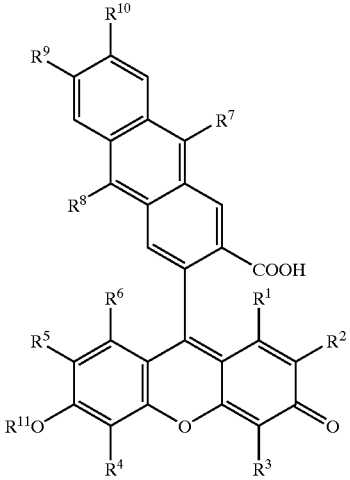

wherein $R^1$, $R^2$, $R^3$, $R^4$, $R^5$, and $R^6$ independently represent a hydrogen atom, a halogen atom, a $C_{1-6}$ alkyl group, or a $C_{1-6}$ alkoxyl group, $R^7$ and $R^8$ independently represent a $C_{1-6}$ alkyl group or an aryl group which may be substituted, $R^9$ and $R^{10}$ independently represent a hydrogen atom, a $C_{1-6}$ alkyl group, or a $C_{1-6}$ alkoxyl group, and $R^{11}$ represents a hydrogen atom or a $C_{1-6}$ alkanoyl group, or salts thereof. The aforementioned compounds are substantially non-fluorescent and react with singlet oxygen under a physiological condition to give a fluorescent substance, and therefore they are useful as agents for measurement of singlet oxygen.

17 Claims, 4 Drawing Sheets

(a)

(b)

(a)

(b)

AGENT FOR MEASUREMENT OF SINGLET OXYGEN

This application is a 371 of PCT/JP99/01658 filed Mar. 31, 1999.

TECHNICAL FIELD

The present invention relates to a compound or a salt thereof useful as an agent for measurement of singlet oxygen. The present invention also relates to an agent for measurement of singlet oxygen comprising the aforementioned compound or a salt thereof.

BACKGROUND ART

It is known that, in living bodies and life phenomena, free radical species such as nitrogen monoxide are acting as a second messenger for signal transduction, and they exert various physiological functions, for example, control of blood pressure in the circulatory system and the like. It has also been shown that superoxides and hydrogen peroxide as active oxygen species also exert important physiological functions in the immune system and the like. However, importance of singlet oxygen as a physiologically active species, which has an analogous electronic structure, has little been elucidated so far.

Recently, singlet oxygen has been revealed to be a reactive species of photodynamic therapy, which is one of cancer therapies, and it has been suggested that various kinds of oxidases, peroxidases and the like are generating singlet oxygen in living bodies. Furthermore, it has also been revealed that oxygen molecules act as a sensor and show signal-like actions, and therefore, singlet oxygen is also suggested to have possible responsibility of important physiological functions in living bodies.

Ten or more different methods are conventionally known as methods for measurement of singlet oxygen in living bodies, which include the chemiluminescence method, the electron spin resonance (ESR) method, the luminescence method and the like. However, these methods in common give only low specificity and sensitivity, and thus they are not reliable methods (as for the method for specific detection of singlet oxygen, see, Nagano, T., et al., Free radicals in Clinical Medicine, Vol. 7, pp.35–41, 1993, etc.). Therefore, it is desired to develop a method for measurement of singlet oxygen superior in specificity and sensitivity to study the involvement of singlet oxygen in life phenomena.

DISCLOSURE OF THE INVENTION

An object of the present invention is to provide a compound useful as an agent for measurement of singlet oxygen. Another object of the present invention is to provide an agent for measurement of singlet oxygen comprising said compound and a method for measurement of singlet oxygen using said compound. In particular, it is an object of the present invention to provide an agent for accurate measurement of singlet oxygen localized in particular cells or tissues in living bodies by a bioimaging technique.

The inventors of the present invention conducted various studies to achieve the foregoing objects. As a result, they found that a substantially non-fluorescent compound represented by the following general formula (I) efficiently reacts with singlet oxygen to give a fluorescent compound represented by the general formula (II). They also found that singlet oxygen can be measured with extremely high specificity and sensitivity by using a compound represented by the general formula (I) as an agent for measurement of singlet oxygen, and measuring fluorescence of a compound of the general formula (II) which is produced as a result of reaction of the compound represented by the general formula (I) and singlet oxygen localized in living cells or tissues. The present invention was achieved on the basis of these findings.

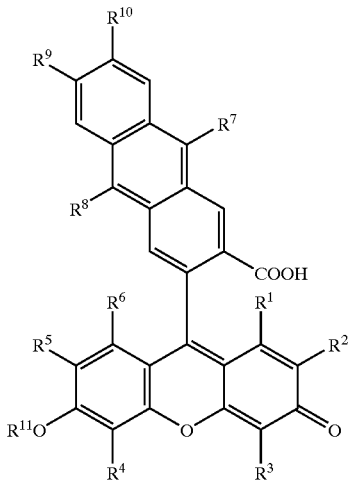

wherein $R^1$, $R^2$, $R^3$, $R^4$, $R^5$ and $R^6$ independently represent a hydrogen atom, a halogen atom, a $C_{1-6}$ alkyl group, or a $C_{1-6}$ alkoxyl group, $R^7$ and R8 independently represent a $C_{1-6}$ alkyl group or an aryl group which may be substituted, $R^9$ and $R^{10}$ independently represent a hydrogen atom, a $C_{1-6}$ alkyl group, or a $C_{1-6}$ alkoxyl group, and $R^{11}$ represents a hydrogen atom or a $C_{1-12}$ alkanoyl group, or salts thereof.

From another aspect of the present invention, there are also provided compounds represented by the following general formula (II):

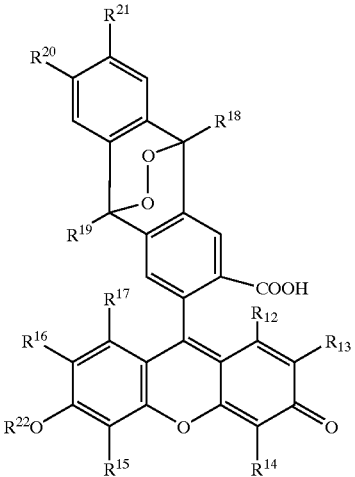

wherein $R^{12}$, $R^{13}$, $R^{14}$, $R^{15}$, $R^{16}$ and $R^{17}$ independently represent a hydrogen atom, a halogen atom, a $C^{1-6}$ alkyl group, or a $C_{1-6}$ alkoxyl group, $R^{18}$ and $R^{19}$ independently represent a $C_{1-6}$ alkyl group or an aryl group which may be substituted, $R^{20}$ and $R^{21}$ independently represent a hydrogen atom, a $C_{1-6}$ alkyl group, or a $C_{1-6}$ alkoxyl group, and $R^{22}$ represents a hydrogen atom or a $C_{1-12}$ alkanoyl group, or salts thereof.

From further aspects of the present invention, there are provided agents for measurement of singlet oxygen comprising a compound represented by the aforementioned formula (I) or a salt thereof; and methods for measuring singlet oxygen, which comprise the steps of: (A) reacting a compound of the aforementioned formula (I) or a salt thereof with singlet oxygen, and (B) measuring fluorescence of a compound of the aforementioned formula (II) or a salt thereof produced in the above step (A).

In addition to the above, there are also provided compounds represented by the following general formula (III):

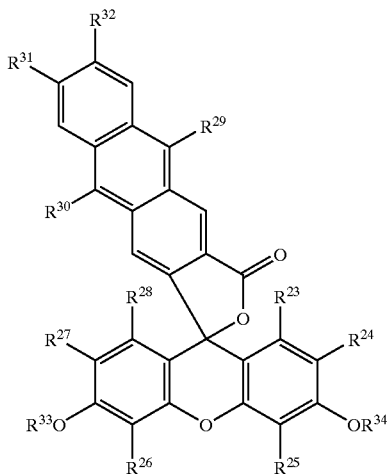

wherein $R^{23}$, $R^{24}$, $R^{25}$, $R^{26}$, $R^{27}$ and $R^{28}$ independently represent a hydrogen atom, a halogen atom, a $C_{1-6}$ alkyl group, or a $C_{1-6}$ alkoxyl group, $R^{29}$ and $R^{30}$ independently represent a $C_{1-6}$ alkyl group or an aryl group which may be substituted, $R^{31}$ and $R^{32}$ independently represent a hydrogen atom, a $C_{1-6}$ alkyl group or a $C_{1-6}$ alkoxyl group, and $R^{33}$ and $R^{34}$ independently represent a $C_{1-12}$ alkanoyl group, and compounds represented by the following general formula (IV):

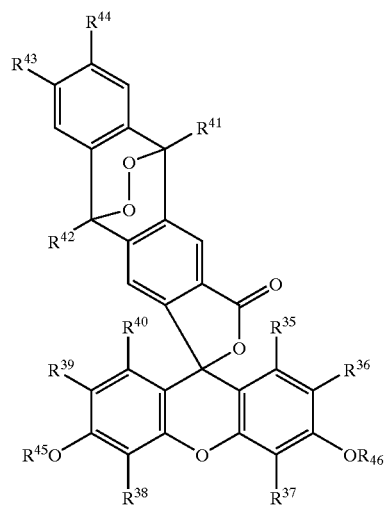

wherein $R^{35}$, $R^{36}$, $R^{37}$, $R^{38}$, $R^{39}$ and $R^{40}$ independently represent a hydrogen atom, a halogen atom, a $C_{1-6}$ alkyl group, or a $C_{1-6}$ alkoxyl group, $R^{41}$ and $R^{42}$ independently represent a $C_{1-6}$ alkyl group or an aryl group which may be substituted, $R^{43}$ and $R^{44}$ independently represent a hydrogen atom, a $C_{1-6}$ alkyl group or a $C_{1-6}$ alkoxyl group, and $R^{45}$ and $R^{46}$ independently represents a $C_{1-12}$ alkanoyl group. The compounds represented by the formula (III) are also useful as agents for measurement of singlet oxygen.

BEST MODE FOR CARRYING OUT THE INVENTION

Figure 1:
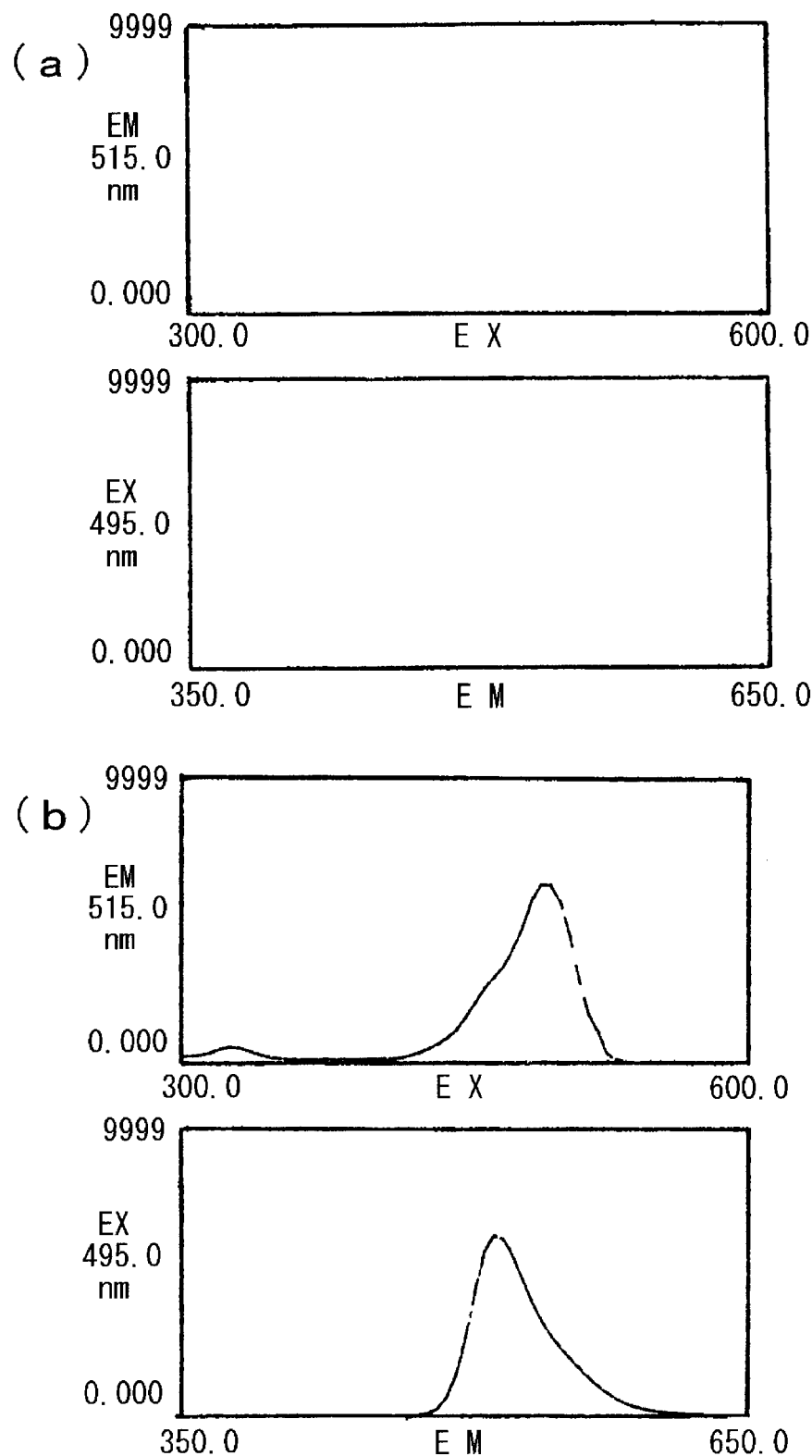
FIG. 1 shows fluorescence spectra of a compound of the formula (I) (Compound 13) and a corresponding compound of formula (II). In the figure, fluorescence spectrum of Compound 13 is shown in (a), and fluorescence spectrum of the corresponding compound of the formula (II) is shown in (b).

The terms used in this specification have the following meanings. An alkyl group or an alkyl moiety of an alkoxyl group may be linear, branched, or cyclic. For example, the term of $C_{1-6}$ alkyl group means a linear, branched, or cyclic alkyl group having 1 to 6 carbon atoms. More specifically, methyl group, ethyl group, n-propyl group, isopropyl group, cyclopropyl group, n-butyl group, sec-butyl group, tert-butyl group, cyclobutyl group, n-pentyl group, n-hexyl group, cyclohexyl group and the like may be used. As the alkyl group and the alkoxyl group, those having a linear or branched chain are preferred. As the halogen atom, any of fluorine atom, chlorine atom, bromine atom, and iodine atom may be used. The alkanoyl group may be either linear or branched. As the alkanoyl group, for example, formyl group, acetyl group, propanoyl group and the like can be used.

As the aryl group, for example, a monocyclic, bicyclic, or tricyclic aryl group having about 6 to 14 ring-constituting atoms can be used. A phenyl group or naphthyl group may preferably be used, and phenyl group may be more preferably used. The aryl group may have one or more substituents on the ring. When the aryl group has two or more substituents, they may be the same or different. The type and substituting position of the substituent are not particularly limited. As the substituent(s), a $C_{1-6}$ alkyl group, a $C_{1-6}$ haloalkyl group, a $C_{1-6}$ alkenyl group, a $C_{1-6}$ alkoxyl group, a halogen atom, a cyano group, a nitro group, an amino group which may be substituted, a carboxyl group, an alkoxycarbonyl group, a $C_{1-6}$ alkanoyl group, a $C_{1-6}$ haloalkanoyl group, an aroyl group, a hydroxyl group, alkylenedioxy group and the like may be used. Among them, a $C_{1-6}$ alkyl group, a $C_{1-6}$ alkoxyl group, a halogen atom and the like are preferred.

In the formula (I), it is preferred that all of $R^1$, $R^3$, $R^4$, and $R^6$ are hydrogen atoms. Further, it is preferred that $R^2$ and $R^5$ independently represent a hydrogen atom or a halogen atom, and it is more preferred that the both are hydrogen atoms or halogen atoms. When $R^2$ and/or $R^5$ represent(s) a halogen atom, chlorine atom is preferred as the halogen atom. It is preferred that $R^7$ and $R^8$ independently represent a phenyl group which may be substituted, and it is more preferred that they are both phenyl groups. $R^{11}$ is preferably a hydrogen atom.

In the formula (II), it is preferred that all of $R^{12}$, $R^{14}$, $R^{15}$, and $R^{17}$ are hydrogen atoms. Further, it is preferred that $R^{13}$ and $R^{16}$ independently represent a hydrogen atom or a halogen atom, and it is more preferred that the both are hydrogen atoms or halogen atoms. When $R^{13}$ and/or $R^{16}$ represent(s) a halogen atom, chlorine atom is preferred as the halogen atom. It is preferred that $R^{18}$ and $R^{19}$ independently represent a phenyl group which may be substituted, and it is more preferred that they are both phenyl groups. $R^{22}$ is preferably a hydrogen atom.

In the formula (III), it is preferred that all of $R^{23}$, $R^{25}$, $R^{26}$, and $R^{28}$ are hydrogen atoms. Further, it is preferred that $R^{24}$ and $R^{27}$ independently represent a hydrogen atom or a halogen atom, and it is more preferred that the both are hydrogen atoms or halogen atoms. When $R^{24}$ and/or $R^{27}$ represent(s) a halogen atom, chlorine atom is preferred as the halogen atom. It is preferred that $R^{29}$ and $R^{30}$ independently represent a phenyl group which may be substituted, and it is more preferred that they are both phenyl groups. It is preferred that both of $R^{33}$ and $R^{34}$ are acetyl groups.

In the formula (IV), it is preferred that all of $R^{35}$, $R^{37}$, $R^{38}$, and $R^{40}$ are hydrogen atoms. Further, it is preferred that $R^{36}$ and $R^{39}$ independently represent a hydrogen atom or a halogen atom, and it is more preferred that the both are hydrogen atoms or halogen atoms. When $R^{36}$ and/or $R^{39}$ represent(s) a halogen atom, chlorine atom is preferred as the halogen atom. It is preferred that $R^{41}$ and $R^{42}$ independently represent a phenyl group which may be substituted, and it is more preferred that they are both phenyl groups. It is preferred that both of $R^{45}$ and $R^{46}$ are acetyl groups.

The compounds of the formula (I) and the formula (II) can exist as a base addition salt. Examples of the base addition salts include, for example, metal salts such as sodium salts, potassium salts, calcium salts, and magnesium salt, ammonium salts, organic amine salts such as triethylamine salts, piperidine salts and morpholine salts and the like. However, salts of the compounds of the present invention are not limited to these examples. Among them, physiologically acceptable water-soluble base addition salts can suitably be used as the agent of the present invention and applied to the method for measurement of the present invention. Further, the compounds of the formula (I) and the formula (II) in free forms or salts thereof may exist as hydrates or solvates, and any of these substances fall within the scope of the present invention. The types of solvents that form the solvates are not particularly limited. For example, solvents such as ethanol, acetone and isopropanol can be exemplified.

The compounds of the formula (I) and the formula (II) may have one or more asymmetric carbons depending on the type of the substituent(s), and optical isomers or diastereoisomers may exist. Further, depending on the nature of $R^1$ and/or $R^6$, or $R^{12}$ and/or $R^{17}$, optical isomers due to rotation hindrance may exist. These isomers in pure forms, any mixtures of these isomers, racemates and the like fall within the scope of the present invention. In addition, the compounds of the formula (I) and the formula (II) of the present invention may form a lactone ring and exist as compounds having a structure corresponding to the fundamental structure of the compounds of the formula (III) or the formula (IV), or they may also exist as other tautomers. It should be recognized that the compounds having the lactone ring formed and other isomers fall within the scope of the present invention. Optically active substances due to the aforementioned lactone formation also fall within the scope of the present invention.

Methods for preparing the compounds of the present invention are not particularly limited. For example, they can be prepared according to the method shown in the following scheme.

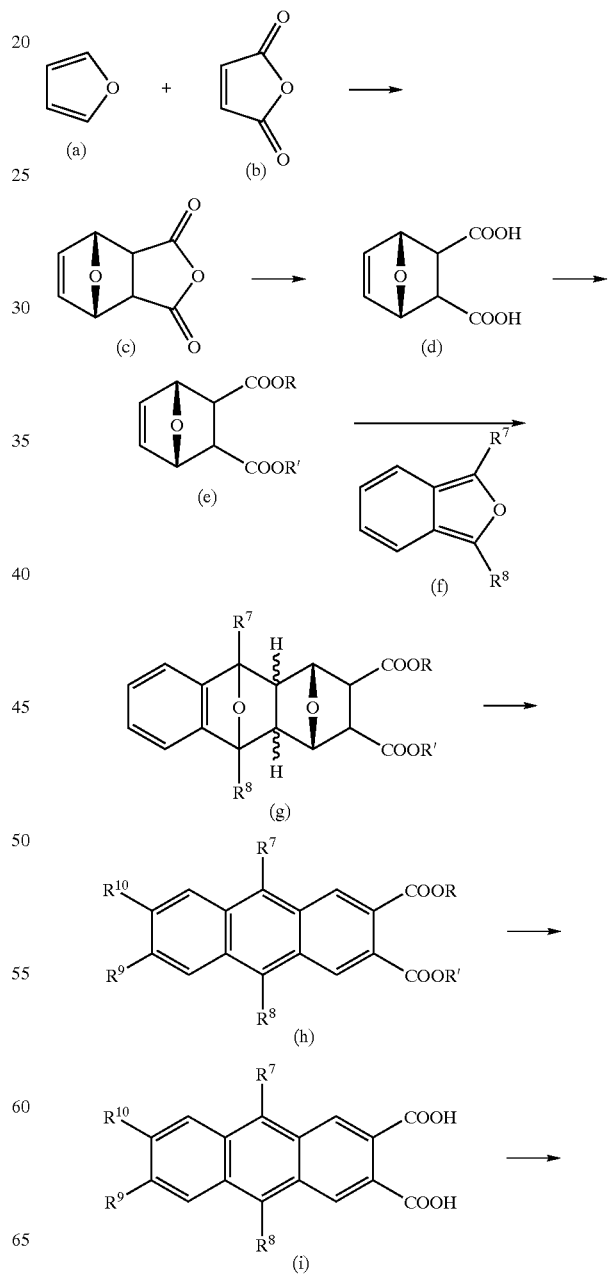

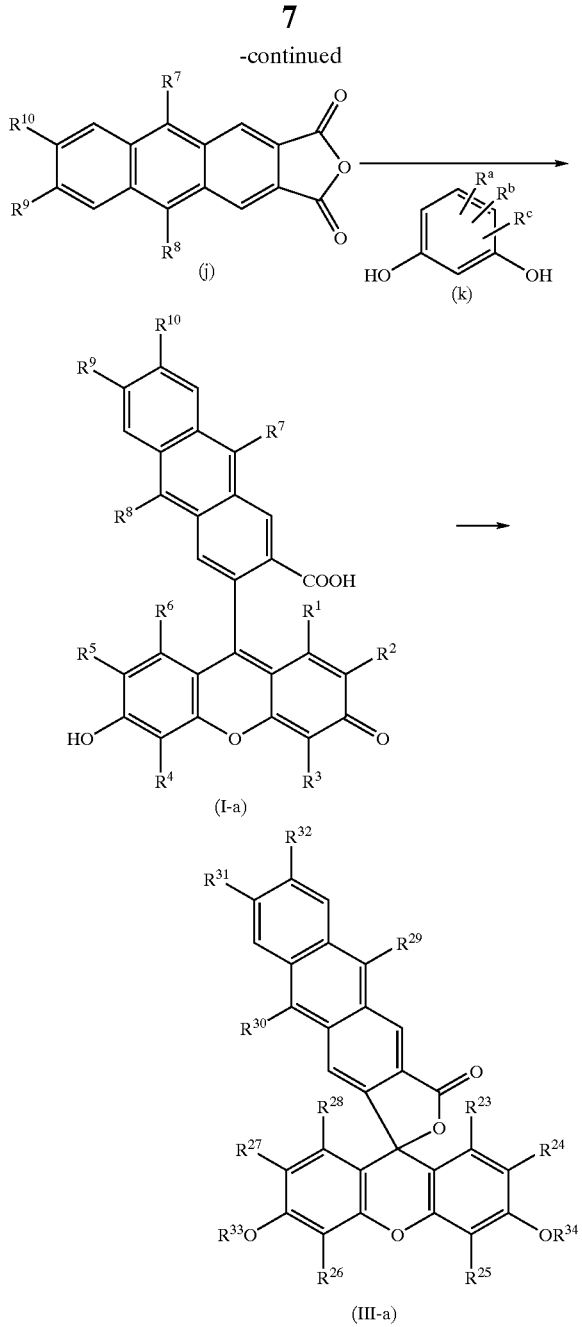

(The symbols used in the scheme have the same meanings as those defined above. R and R' independently represent a protective group of carboxyl group, and $R^a$, $R^b$, and $R^c$ independently represent a hydrogen atom, a halogen atom, a $C_{1-6}$ alkyl group, or a $C_{1-6}$ alkoxy group.)

Compound (d) can be prepared by adding water to Compound (c), which is obtained by reacting maleic anhydride (b) with furan (a). After the carboxyl group of Compound (d) is protected with a suitable protective group, the resulting compound can be reacted with Compound (f) to prepare Compound (g).

The protective group of the carboxyl group of Compound (d) is not particularly limited so long as the group is inactive in reactions directed to other functional groups and can be eliminated by suitable means as required. For example, a lower alkyl ester (methyl ester etc.) can be used. When methyl ester of Compound (d) is produced, for example, Compound (d) can be reacted with methyl iodide in the presence of a solvent such as acetone, or without solvent. It is preferable to carry out the reaction with addition of a base such as cesium carbonate.

In accordance with the method described in Tetrahedron 38, pp.1425–1430 (1982), Compound (f) can be reacted with the compound (e) to prepare Compound (g), which can then be treated with an acid to prepare Compound (h). The reaction can be carried out in the presence of a solvent such as chloroform with warming. Compound (f) can be readily produced in accordance with, for example, the method described in Tetrahedron 38, pp.1425–1430 (1982).

The conversion reaction from Compound (g) to Compound (h) can generally be carried out in an inert solvent such as methylene chloride. The reaction can be performed by adding an acid such as sulfuric acid to a solution of Compound (g) and vigorously stirring the mixture. Apart from the aforementioned method, Compound (h) can also be prepared according to the method described in Tetrahedron 39, pp.623–627 (1983) or Can. J. Chem., 53, pp.256–262 (1975).

Then, the protective group of the carboxyl group can be eliminated from the resulting Compound (h) to prepare Compound (i), from which the acid anhydride (j) can then be prepared.

The deprotection of the carboxyl group can be performed with a reaction suitably selected depending on the nature of the protective group. For example, cleavage of a lower alkyl ester such as methyl ester can be attained by treating Compound (h) with an alkali such as methanolic potassium hydroxide in the presence of an inert solvent such as dioxane. This reaction can be performed generally at room temperature or with heating, preferably under reflux of the solvent with heating.

The dehydration of Compound (i) can be performed by adding a dehydrating agent to Compound (i) in the presence of an inactive solvent generally from a hot temperature to a refluxing temperature of the solvent. The kind of the dehydrating agent is not particularly limited and those skilled in the art can suitably choose the agent. For example, acetic anhydride may be used, which serves also as the solvent.

Compound (j) and Compound (k) can be reacted to prepare a compound of the present invention represented by the formula (I-a). The reaction can be performed by melting the reactants in the presence of a Lewis acid such as zinc chloride and boron trifluoride without a solvent, or reacting Compound (i) with Compound (k) in methanesulfonic acid without using zinc chloride. When $R^{10}$ and/or $R^{11}$ represent(s) a $C_{1-6}$ alkoxyl group, it is preferable to react Compound (i) with Compound (k) in methanesulfonic acid without using zinc chloride. Compound (k), a resorcinol derivative, is a known compound, per se, and the compound can be readily prepared. Further, a compound of the formula (I) whose $R^{11}$ is an alkanoyl group can be prepared by reacting one equivalence of an acylating agent with Compound (I-a), and a compound of the formula (III-a) can be prepared by reacting two equivalences or more of an acylating agent with the compound (I-a). Where acetylation is performed, an ordinary acetylating agent such as acetic anhydride and pyridine can be used, and the reaction can be carried out at room temperature or with heating.

The compound represented by the formula (II) can be prepared by reacting hydrogen peroxide, generated in a solution containing a salt such as sodium molybdate ($Na_2MoO_4$), with a compound of the formula (I) which can be prepared as described above.

The method for preparing the compounds of the present invention will be described more specifically and in more detail in examples of the specification. Therefore, those skilled in the art can prepare any of the compounds of the present invention by referring to the explanations of the manufacturing method mentioned in the above schemes and specific explanations in the examples, and by appropriately choosing starting materials and reagents, and by suitably altering or modifying reaction conditions, reaction steps and the like as required.

A target compound can sometimes be efficiently prepared by performing the reaction after protection of a certain functional group as required in the aforementioned reaction steps. Detailed explanations of protective groups are given in, for example, Protective Groups in Organic Synthesis, T. W. Greene, John Wiley & Sons, Inc., 1981 and the like, and those skilled in the art can choose suitable protective groups.

In the above preparations, isolation and purification of the products can be performed by a suitable combination of techniques used for usual organic synthesis, for example, filtration, extraction, washing, dehydration, concentration, crystallization, various chromatography techniques and the like. The synthetic intermediates in the aforementioned steps can be used for the subsequent reactions without particular purification. Where preparation of a salt of the compound of the present invention is desired, when a salt of each compound is obtained in the above preparation, the resulting salt, per se, may be purified. When a compound in a free form is obtained, the compound in a free form can be dissolved or suspended in a suitable solvent and added with a base to form a salt, which may be purified as required.

The compounds represented by the aforementioned formula (I) and salts thereof have a property that they react with singlet oxygen under a mild condition, for example, a physiological condition, to give a corresponding compound of the aforementioned formula (II) or a salt thereof. The compounds of the formula (I) and salts thereof are substantially non-fluorescent, whereas the compounds of the formula (II) and salts thereof have a property of emitting fluorescence of high intensity. Therefore, by subjecting a compound of the aforementioned formula (I) or a salt thereof to reaction with singlet oxygen, and then measuring fluorescence of a produced compound of the aforementioned formula (II), singlet oxygen can be measured. The compounds of the formula (I) or salts thereof have a property that they do not substantially react with oxygen radicals and the like, but specifically react with singlet oxygen. Further, the compounds of the formula (II) and salts thereof have extremely superior fluorescence intensity. Therefore, singlet oxygen localized in individual cells or particular tissues can be accurately measured by using the compound of the formula (I) or a salt thereof as an agent for measurement of singlet oxygen.

The term "measurement" used in the present specification must be construed in its broadest sense, including measurements performed for the purpose of quantification, qualification, diagnosis or the like, as well as tests or detections and the like. The method for measurement of singlet oxygen of the present invention generally comprises the steps of (A) reacting a compound of the aforementioned formula (I) or a salt thereof with singlet oxygen, and (B) measuring fluorescence of a compound of the aforementioned formula (II) or a salt thereof produced in the above step (A). The fluorescence of the compound of the aforementioned formula (II) or a salt thereof may be measured by a usual method. A method of measuring fluorescence spectrum in vitro, a method of measuring fluorescence spectrum in vivo by using a bioimaging technique and the like may be employed. For example, when quantification is desired, it is preferred to prepare a calibration curve beforehand according to a conventional method. As a quantitative singlet oxygen generation system, for example, the naphthalene endoperoxide system (Saito, I, .et al., J. Am. Chem. Soc., 107,pp.6329–6334, 1985) and the like can be used.

A compound of the formula (I) wherein $R^{11}$ is a $C_{1-12}$ alkanoyl group or a salt thereof, or a compound of the formula (III) gives a product, after it passes through a cell membrane and is taken up into a cell, in which the alkanoyl group is hydrolyzed by an enzyme such as an intracellular esterase [a compound of the formula (I) wherein $R^{11}$ is a hydrogen atom or a salt thereof]. The hydrolysis product reacts with singlet oxygen in the cell without being easily excreted out of the cell to give a compound of the formula (II) wherein $R^{22}$ is a hydrogen atom. Therefore, if these compounds are used as agents for the measurement, singlet oxygen localized in individual cells can be measured by a bioimaging technique with high sensitivity.

As the agent for measurement of singlet oxygen of the present invention, a compound of the formula (I) or a salt thereof or a compound of the aforementioned formula (III) per se may be used. They may also be used as a composition formulated with additives ordinarily used for preparation of agents, if desired. For example, as additives for use of the agent in a physiological condition, additives such as dissolving aids, pH modifiers, buffers, isotonic agents and the like can be used, and amounts of these additives can suitably be chosen by those skilled in the art. The compositions may be provided compositions in appropriate forms, for example, powdery mixtures, lyophilized products, granules, tablets, solutions and the like.

EXAMPLES

The present invention will be more specifically explained with reference to the following examples. However, the scope of the present invention is not limited to the following examples. The compound numbers in the following schemes correspond to those used in the examples.

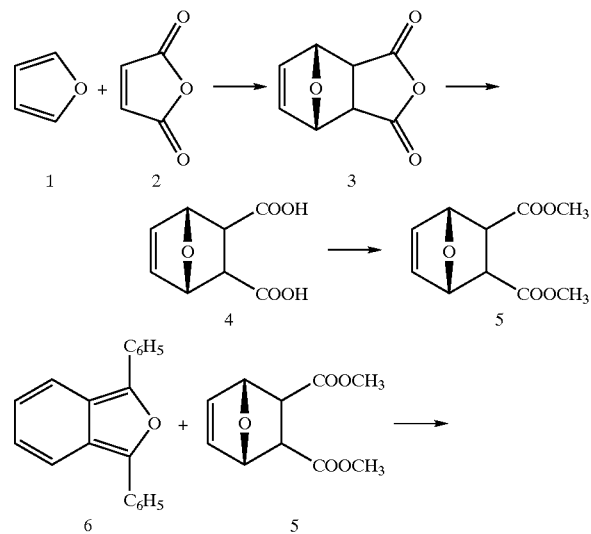

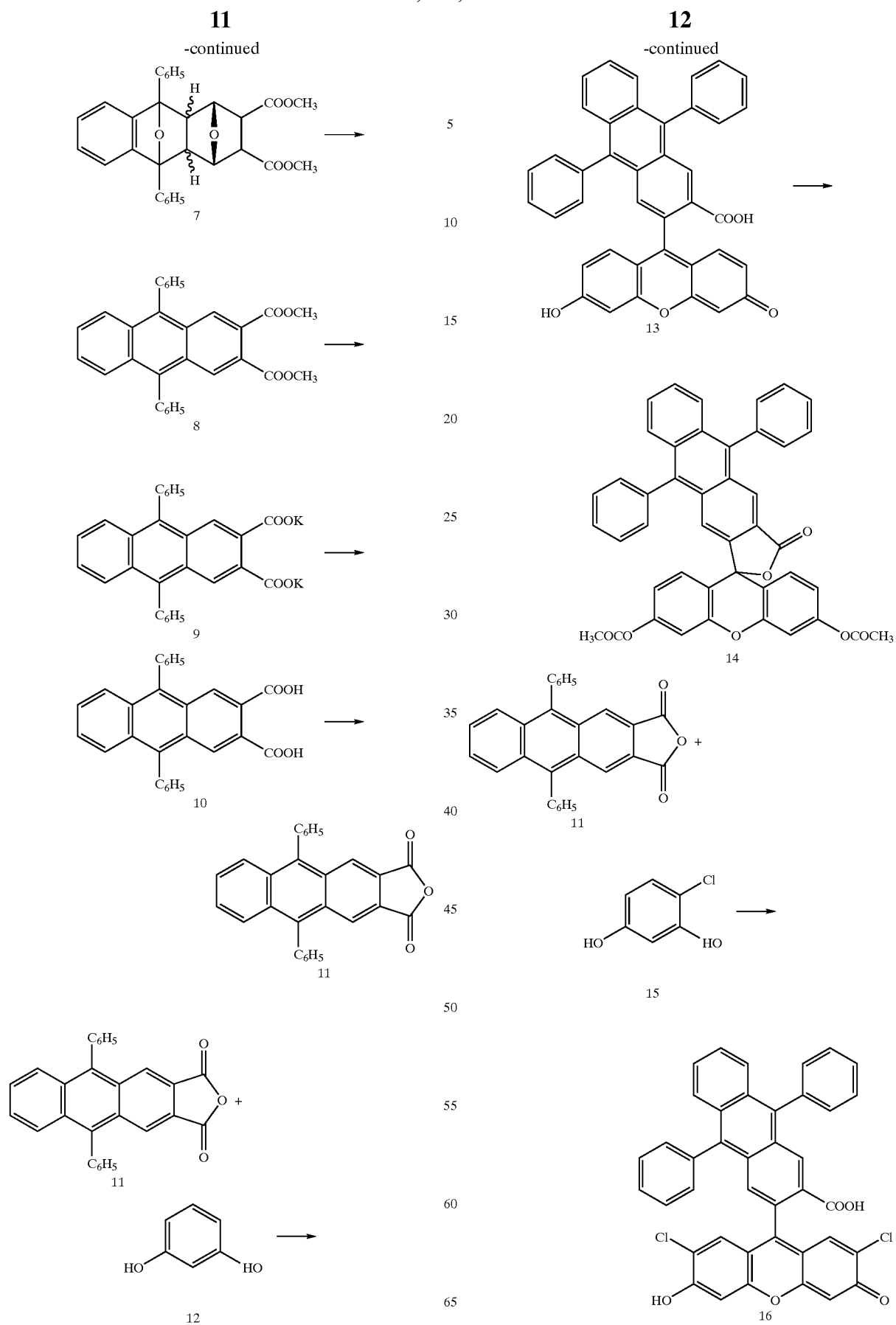

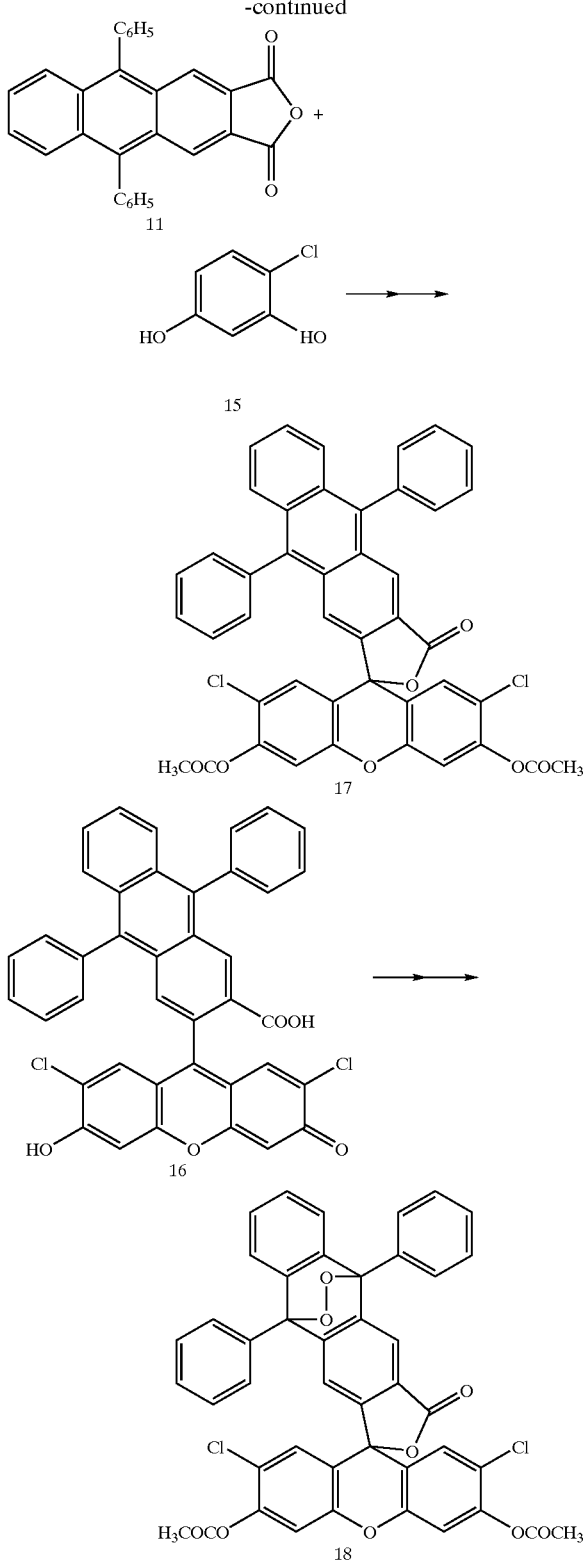

Example 1

Preparation of compounds

Maleic anhydride (2) pulverized into powder was dissolved in tetrahydrofuran (THF), added with 1.05 equivalences of distilled fresh furan (1) and stirred for ten days at room temperature. The deposited crystals were collected by filtration to obtain Compound (3) (colorless crystals, yield: 46%).

$^1$H NMR (300 MHz, CDCl$_3$): δ3.18 (s, 2H), 5.46 (m, 2H), 6.58 (m, 2H)

MS (EI$^+$): 121(M$^+$-COOH)

m.p.: 120–122° C.

Compound (3) was suspended in water and stirred at room temperature for 2 hours. The suspension gradually turned into a transparent solution. Water was removed by lyophilization to obtain Compound (4) (colorless powder, yield: 100%).

$^1$H NMR (300 MHz, DMSO): δ2.61 (s, 2H), 5.03 (m, 2H), 6.43 (m, 2H)

m.p.: 134° C.

An acetone solution of Compound (4) was added with 6 equivalences of methyl iodide and 1.1 equivalences of cesium carbonate, and stirred for seven days at room temperature. The reaction mixture was filtered under reduced pressure, and the insoluble solids were sufficiently washed with methylene chloride. The resulting organic layer was concentrated under reduced pressure and washed with saturated brine. The organic layer was dried over sodium sulfate, and the solvent was evaporated under reduced pressure to obtain a crude product. The crude product was recrystallized from methanol to obtain Compound (5) (colorless plates, yield: 56%).

$^1$H NMR (300 MHz, CDCl$_3$): δ2.83 (s, 2H), 3.71 (s, 6H), 5.27 (m, 2H), 6.46 (m, 2H)

MS (FAB$^+$): 213 (M$^+$+1)

m.p.: 121° C.

Anal. Calcd. for C$_{10}$H$_{12}$O$_5$: C, 56.60%; H, 5.70%.

Found: C, 56.32%; H, 5.66%.

A chloroform solution of one equivalence of Compound (6) and 1.05 equivalences of Compound (5) was refluxed by heating under argon atmosphere for two days. After chloroform was evaporated under reduced pressure, the residue was added with isopropyl ether, and the precipitates were collected by filtration. The precipitates were washed with pentane to obtain Compound (7) (colorless powder, yield: 100%). Measurement of $^1$H NMR (300 MHz, CDCl$_{13}$) revealed that the product was a mixture of two isomers (mixing ratio of isomers: 75/25).

1st Isomer

δ2.59 (s, 2H), 2.90 (s, 2H), 3.55 (s, 6H), 4.60 (s, 2H), 7.14 (s, 4H), 7.4–7.7 (m, 10H)

2nd Isomer

δ3.01 and 3.04 (2s, 2H), 3.64 (s, 6H), 4.65 (s, 2H), 7.14 (s, 4H), 7.4–7.7 (m, 10H)

MS (EI$^+$): 482 (M$^+$weak), 451 (M$^+$-CH$_3$O)

m.p.: 237° C. (decomp.)

A methylene chloride solution of the compound (7) was added with concentrated sulfuric acid and refluxed by heating for 30 minutes with vigorous stirring. After treatment with methanol, the organic layer was washed with a saturated sodium hydrogencarbonate solution. The organic layer was dried over magnesium sulfate, and the solvent was evaporated under reduced pressured to obtain a crude product. The product was purified by silica gel chromatography and then recrystallized from methanol to obtain Compound (8) (yellow needles, yield: 43%).

$^1$NMR (300 MHz, CDCl$_3$): δ3.85 (s, 6H), 7.40–7.74 (m, 14H), 8.13 (s, 2H)

MS (EI$^+$): 446 (M$^+$), 415 (M$^+$-CH$_3$O)

m.p.: 200–201° C.

Anal. Calcd. for C$_{30}$H$_{22}$O$_4$: C, 80.70%; H, 4.97%.

Found: C, 80.44%; H, 4.74%

A dioxane solution of Compound (8) was added with 1 M methanolic potassium hydroxide, and refluxed by heating for 30 minutes. The reaction mixture was cooled, and the precipitates were collected by filtration and washed with anhydrous methanol to obtain Compound (9) (light yellow powder, yield: 91%).

$^1$H NMR (300 MHz, D$_2$O): δ7.29–7.63 (m, 14H), 7.69 (s, 2H)

MS (FAB$^+$): 495(M$^+$+1)

m.p.: 300° C. or higher

A solution in which Compound (9) was suspended in water was made acidic by addition of 2 N hydrochloric acid, and the product was extracted with ether. The ether layer was washed with saturated brine and dried over magnesium sulfate. The solvent was evaporated under reduced pressure to obtain Compound (10) (yellow powder, yield: 100%).

$^1$H NMR (300 MHz, DMSO): δ7.49–7.72 (m, 14H), 7.95 (s, 2H)

MS (EI$^+$): 418 (M$^+$; weak), 400 (M$^+$–H$_2$O)

Compound (10) was added with large excess of acetic anhydride and refluxed by heating for 10 minutes. The reaction mixture was cooled, and the deposited crystals were taken by filtration to obtain Compound (11) (yellow crystals, yield: 96%).

$^1$H NMR (300 MHz, CDCl$_3$): δ7.45–7.80 (m, 14H), 8.46 (s, 2H)

MS (EI$^+$): 400 (M$^+$)

m.p.: 300° C. or higher

Anal. Calcd. for C$_{28}$H$_{16}$O$_3$: C, 83.99%; H, 4.02%.

Found: C, 84.27%; H, 3.99%

One equivalence of the compound (11), two equivalences of resorcinol (12) and one equivalence of zinc chloride were mixed sufficiently. This mixture was heated as solid at 180° C. for 1 hour under argon atmosphere. After cooling, the product was pulverized, added with 2 N hydrochloric acid, and refluxed by heating for 10 minutes. The precipitates were collected by filtration to obtain a crude product. The product was purified by silica gel chromatography to obtain Compound (13) (orange powder, yield: 48%).

$^1$H NMR (300 MHz, DMSO): δ6.46 (dd, 2H, Ja=8.8, Jb=2.1), 6.57 (m, 2H), 6.66 (d, 2H, J=8.8), 7.28 (s, 1H), 7.34–7.77 (m, 14H), 8.24 (s, 1H)

MS (EI$^+$): 584 (M$^+$), 540(M$^+$–CO$_2$)

m.p.: 270° C.

Compound (13) was added with acetic anhydride and pyridine, and stirred for 5 minutes at room temperature. The reaction mixture was poured into 2% hydrochloric acid at 0° C., and extracted with methylene chloride. The organic layer was washed with 2% sodium hydroxide and saturated brine, and then dried over sodium sulfate. The methylene chloride was evaporated under reduced pressure to obtain a crude product, and the product was recrystallized from benzene to obtain Compound (14) (yellow crystals, yield: 67%).

$^1$H NMR (300 MHz, DMSO): δ2.26 (s, 6H), 6.91 (dd, 2H, Ja=8.7, Jb=2.2), 6.98 (d, 2H, J=8.7), 7.24 (d, 2H, J=2.2), 7.30–7.80 (m, 15H), 8.30 (d, 1H, J=0.72)

MS (EI$^+$): 668 (M$^+$), 624 (M$^+$–CO$_2$)

Anal. Calcd. for C$_{44}$H$_{28}$O$_7$: C, 79.03%; H, 4.22%.

Found: C, 79.27%; H, 4.19%.

m.p.: 235° C.

A methanesulfonic acid solution of one equivalence of the compound (11) was added with two equivalences of chlororesorcinol (15) and heated at 80° C. for two days under argon atmosphere. The cooled reaction mixture was poured into ice water, and the precipitates were collected by filtration. The precipitates were dried and purified by silica gel chromatography to obtain Compound (16) (orange powder, yield: 59%).

$^1$H NMR (300 MHz, DMSO): δ6.80 (s, 2H), 6.84 (s, 2H), 7.31–7.78 (m, 15H), 8.28 (s, 1H), 11.14 (s, 2H)

MS (FAB$^+$): 653:655:657=9:6:1 (M$^+$+1)

m.p.: 243° C. (decomp.)

A methanesulfonic acid solution of one equivalence of Compound (11) was added with two equivalences of chlororesorcinol (15) and heated at 80° C. for two days under argon atmosphere. The cooled reaction mixture was poured into ice water, and the precipitates were collected by filtration. The precipitates were added with acetic anhydride and pyridine, and stirred at 80° C. for 5 minutes. The reaction mixture was poured into 2% hydrochloric acid at 0° C. and extracted with methylene chloride. The organic layer was washed with 2% sodium hydroxide and saturated brine, and then dried over sodium sulfate. The methylene chloride was evaporated under reduced pressure to obtain a crude product. The product was purified by silica gel chromatography and recrystallized from benzene to obtain Compound (17) (yellow crystals, yield: 16%).

$^1$H NMR (300 MHz, CDCl$_3$): δ2.36 (s, 6H), 6.88 (s, 2H), 7.12 (s, 2H), 7.35–7.79 (m, 15H), 8.61 (s, 1H)

MS (FAB$^+$): 737:739:741=9:6:1 (M$^+$+1)

m.p.: 246° C. (decomp.)

Anal. Calcd. for C$_{44}$H$_{26}$Cl$_2$O$_7$: C, 71.65%; H, 3.55%.

Found: C, 71.69%; H, 3.48%

A dimethyl sulfoxide (DMSO) solution of Compound (16) was mixed with an aqueous solution containing sodium hydroxide, sodium hydrogencarbonate, sodium carbonate and sodium molybdate (Na$_2$MoO$_4$). This mixture was added with 30% aqueous hydrogen peroxide 5 times while the mixture was appropriately cooled to prevent undesired raise of reaction temperature. The reaction mixture was made acidic with phosphoric acid and then extracted with ether. The organic layer was washed with saturated brine and dried over magnesium sulfate, and ether was evaporated under reduced pressure. The resulting solid was added with acetic anhydride and pyridine and stirred at room temperature for 5 minutes. Then, the reaction mixture was poured into 2% hydrochloric acid at 0° C., and extracted with methylene chloride. The organic layer was washed with 2% sodium hydroxide and saturated brine and then dried over sodium sulfate, and the solvent was evaporated under reduced pressure to obtain a crude product. The product was purified by silica gel chromatography to obtain Compound (18) (light yellow powder, yield: 36%).

$^1$H NMR (300 MHz, CDCl$_3$): δ2.34 (s, 3H), 2.38 (s, 3H), 6.74, 6.80, 7.08, 7.13 (4s, 4H), 7.04–7.78 (m, 15H), 7.84(s, 1H)

MS (FAB$^+$): 769:771:773=9:6:1 (M$^+$+1); 737:739:741=9:6:1 (M$^+$+1–O$_2$)

m.p.: 189° C. (decomp.)

Example 2

Measurement of Singlet Oxygen

The compound (13) obtained in Example 1 was dissolved in 100 mM phosphate buffer (pH 10.5) containing 0.1 mM ethylenediaminetetraacetic acid (EDTA). The solution was then added with Na$_2$MoO$_4$ (1 mM) and DMSO (0.1%), and fluorescence spectrum was measured at 25° C. (FIG. 1(a)). The mixture was added with aqueous hydrogen peroxide (20 mM) five times with an interval of 1 hour, and fluorescence was measured (6 hours after the start of the reaction) (FIG. 1(b)). The conditions of the fluorescence measurement were as follows: excitation wavelength: 495.0 nm; emission wavelength: 515.0 nm; slit (Ex/Em): 2.5 nm/2.5 nm.

Example 3

Measurement of Singlet Oxygen

Figure 2:
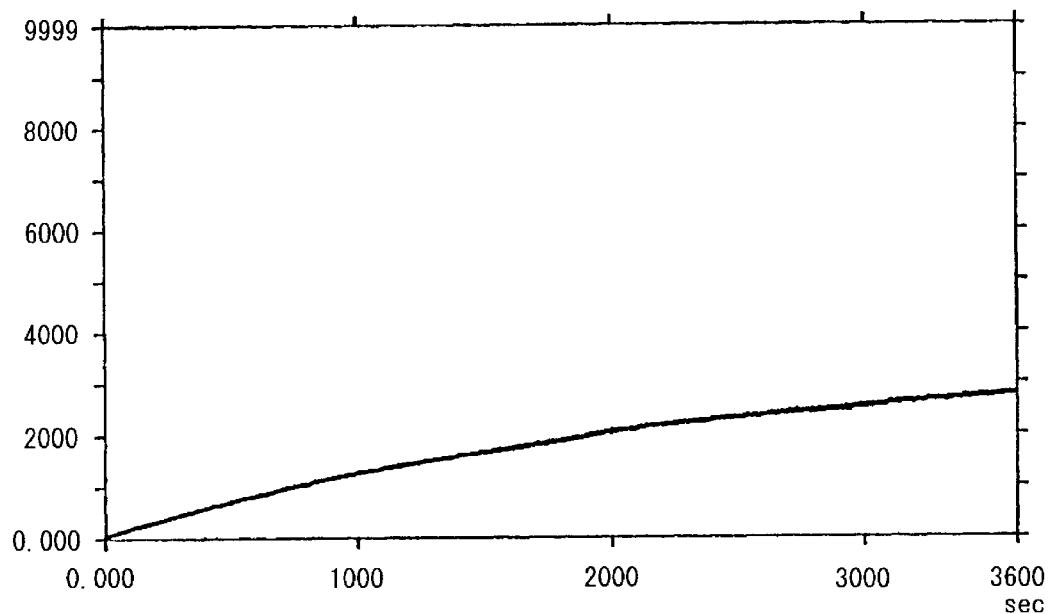
FIG. 2 shows results of time course measurement of change in fluorescence when singlet oxygen was generated in the presence of the Compound 13. In the figure, results obtained in the presence of singlet oxygen are shown in (a), and the results obtained in the absence of singlet oxygen (no addition of $Na_2MoO_4$) are shown in (b).
Figure 2:
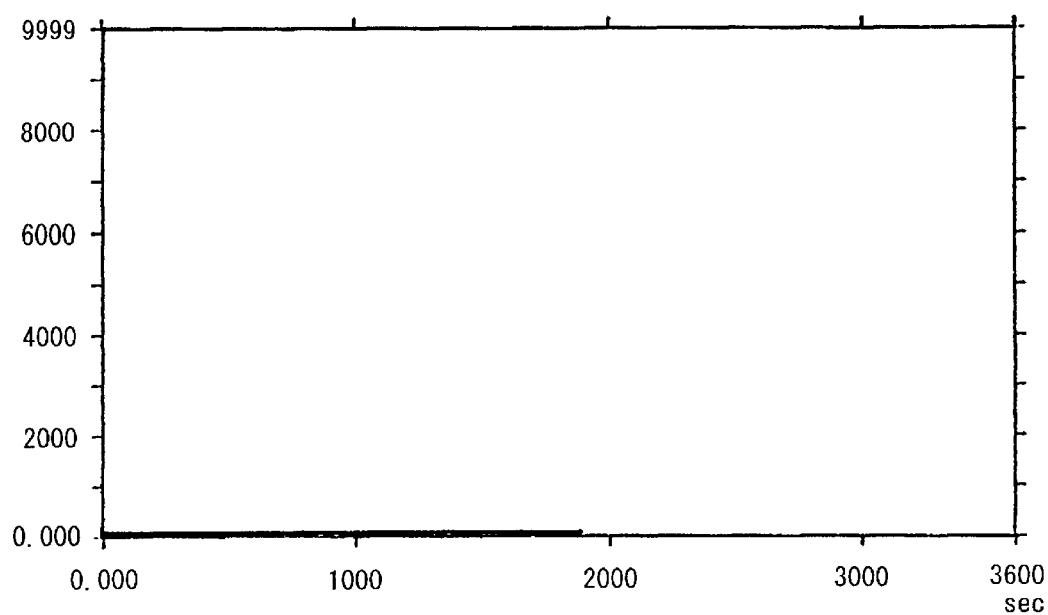

By using a singlet oxygen generation system [0.1 mM EDTA; 100 mM phosphate buffer (pH 10.5); Na$_2$MoO$_4$ (1 mM); DMSO (0.1%); aqueous hydrogen peroxide (20 mM×1); 25° C.], change of fluorescence was measured in the presence of Compound (13) in a time course (FIG. 2(a)). As a control, the measurement was performed without addition of Na$_2$MoO$_4$ (in the absence of singlet oxygen) (FIG. 2(b)). As a result, increase of the fluorescence according to the generated amount of singlet oxygen was observed.

Figure 3:
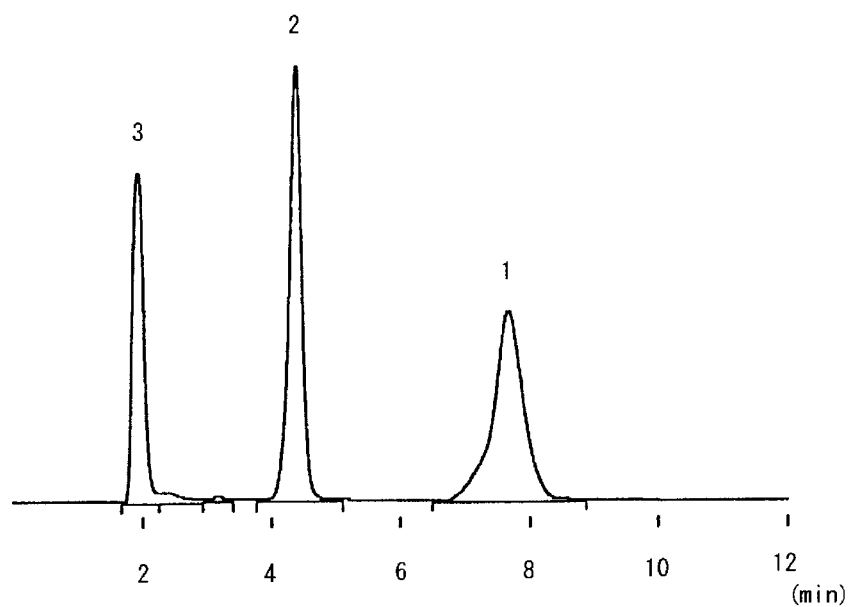
FIG. 3 shows results of high performance liquid chromatography analysis of a reaction mixture in which singlet oxygen was generated in the presence of the Compound 16 (30 minutes after the start of the reaction). In the figure, the results obtained in the presence of singlet oxygen are shown in (a), and the results obtained in the absence of singlet oxygen (no addition of $H_2O_2$) are shown in (b). Peak 1 indicates Compound 16, Peak 2 indicates the corresponding compound of the formula (II), and Peak 3 indicates the front end of the solvent.
Figure 3:
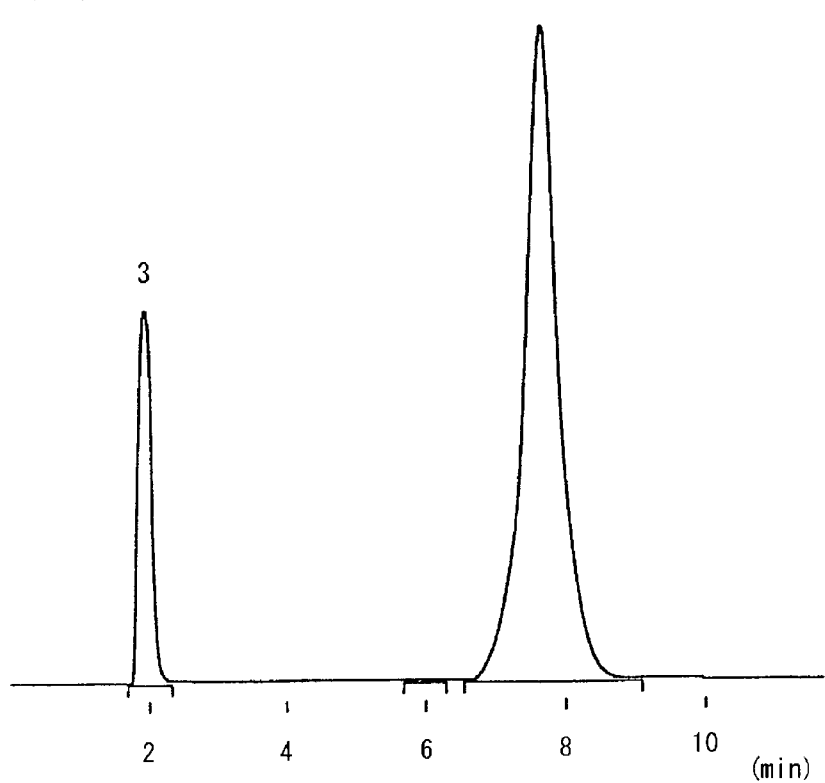

Measurement was also performed in a system substantially same as the above (31 mM NaOH; 16 mM NaHCO$_3$;

1 mM $Na_2CO_3$; 138 mM $Na_2MoO_4$) by using the Compound (16), and the reaction mixture was analyzed by high performance liquid chromatography before the start of reaction and after two times of hydrogen peroxide addition with an interval of 15 minutes (30 minutes after the start of the reaction). The results are shown in FIG. 3. The measurement conditions of the high performance liquid chromatography were as follows.
Column: Inertsil ODS
Eluent: 10 mM phosphate buffer (pH 7.4)/acetonitrile 6/4
Column temperature: room temperature
Detection: 505 nm Example 4

Measurement of Singlet Oxygen

Figure 4:
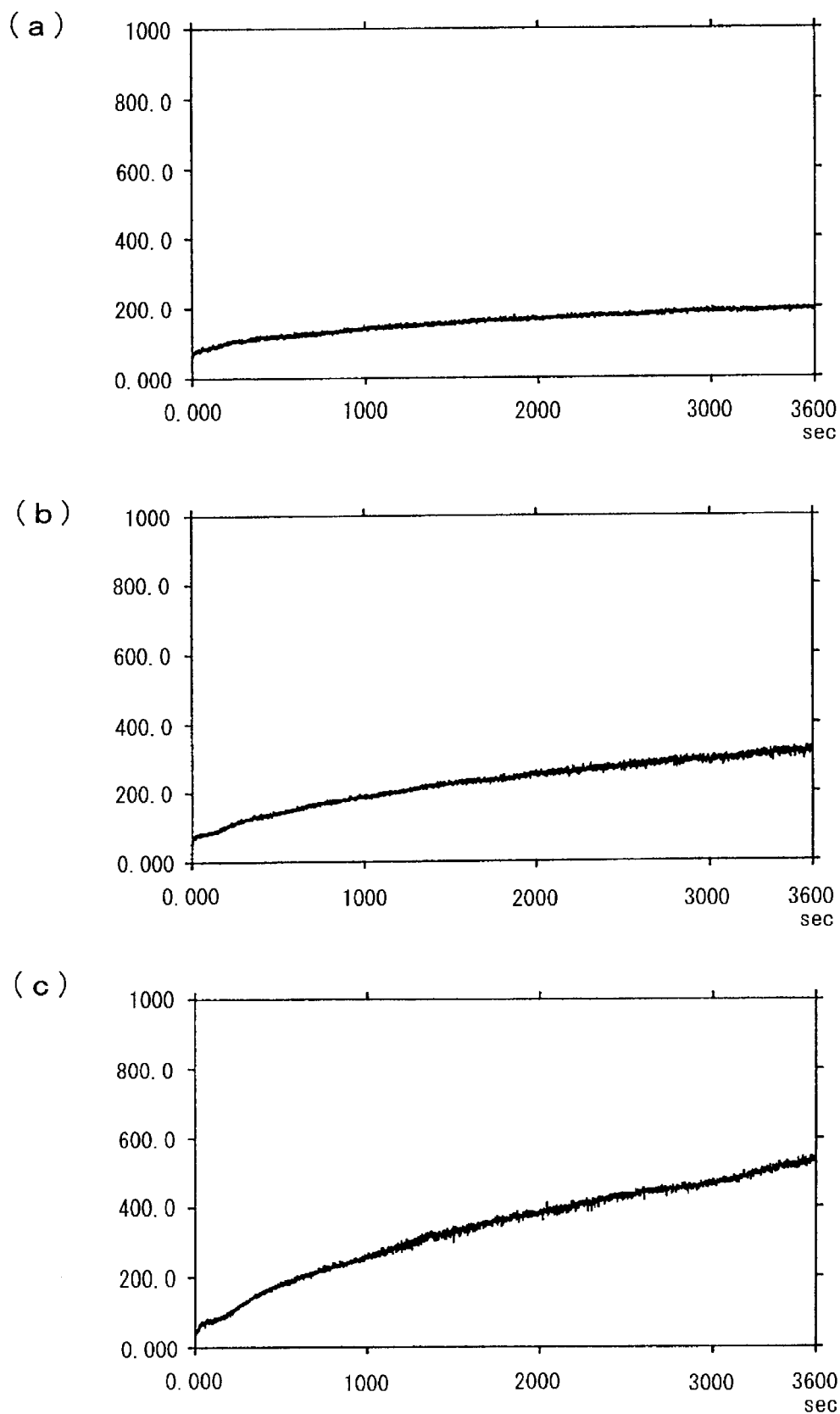
FIG. 4 shows results of time course measurement of change in fluorescence when singlet oxygen was generated under a physiological condition in the presence of Compound 13. In the figure, results obtained in the presence of 1 mM EP-1 are shown in (a), results obtained in the presence of 2.5 mM EP-1 are shown in (b), and results obtained in the presence of 5 mM EP-1 are shown in (c).

Singlet oxygen was generated continuously with time under a neutral condition at 37° C. in given amounts by using a naphthalene endoperoxide compound EP-1 (Saito, I, .et al., J. Am. Chem. Soc., 107, pp.6329–6334, 1985) as a singlet oxygen generation system, and fluorescence was measured in the presence of the compound (13) [reaction mixture: 0.1 mM EDTA; 100 mM phosphate buffer (pH 7.4); DMSO (0.1%)]. As a result, increase of fluorescence intensity according to the generated amount of singlet oxygen was observed as the concentration of EP-1 was increased from 1 mM to 2.5 mM and 5 mM (FIG. 4).

Industrial Applicability

The substantially non-fluorescent compounds represented by the general formula (I) or the general formula (III) and salts thereof according to the present invention efficiently react with singlet oxygen to give a fluorescent compound represented by the general formula (II) or a salt thereof. Therefore, by using the compound represented by the general formula (I) or the general formula (III) or a salt thereof as an agent for measurement of singlet oxygen, and by measuring fluorescence of a compound represented by the general formula (II) or general formula (IV) produced by the reaction with singlet oxygen localized in living cells or tissues, singlet oxygen can be measured with extremely high specificity and sensitivity, for example, through a bioimaging technique.

What is claimed is:

1. A compound represented by the following general formula (I):

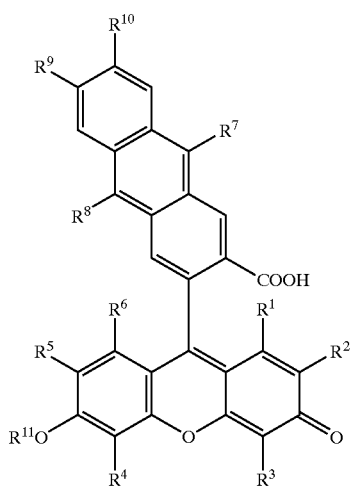

wherein $R^1$, $R^2$, $R^3$, $R^4$, $R^5$, and $R^6$ independently represent a hydrogen atom, a halogen atom, a $C_{1-6}$ alkyl group, or a $C_{1-6}$ alkoxyl group, $R^7$ and $R^8$ independently represent a $C_{1-6}$ alkyl group or an aryl group which may be substituted, $R^9$ and $R^{10}$ independently represent a hydrogen atom, a $C_{1-6}$ alkyl group, or a $C_{1-6}$ alkoxyl group, and $R^{11}$ represents a hydrogen atom or a $C_{1-12}$ alkanoyl group, or a salt thereof.

2. The compound or a salt thereof according to claim 1, wherein $R^1$, $R^3$, $R^4$, and $R^6$ represent a hydrogen atom, $R^2$ and $R^5$ independently represent a halogen atom, $R^7$ and $R^8$ independently represent a phenyl group which may be substituted, and $R^{11}$ represents a hydrogen atom.

3. The compound or a salt thereof according to claim 1, wherein $R^1$, $R^3$, $R^4$, and $R^6$ represent a hydrogen atom, $R^2$ and $R^5$ represent a chlorine atom, $R^7$ and $R^8$ represent a phenyl group, and $R^{11}$ represents a hydrogen atom.

4. A compound represented by the following general formula (II):

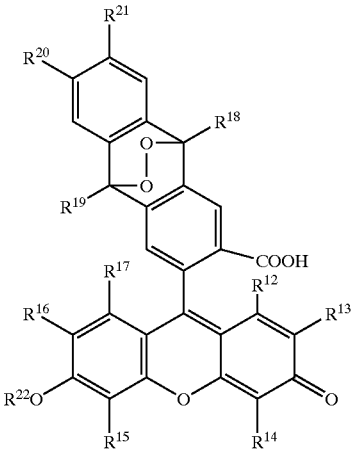

wherein $R^{12}$, $R^{13}$, $R^{14}$, $R^{15}$, $R^{16}$, and $R^{17}$ independently represent a hydrogen atom, a halogen atom, a $C_{1-6}$ alkyl group, or a $C_{1-6}$ alkoxyl group, $R^{18}$ and $R^{19}$ independently represent a $C_{1-6}$ alkyl group or an aryl group which may be substituted, $R^{20}$ and $R^{21}$ independently represent a hydrogen atom, a $C_{1-6}$ alkyl group, or a $C_{1-6}$ alkoxyl group, and $R^{22}$ represents a hydrogen atom or a $C_{1-12}$ alkanoyl group, or a salt thereof.

5. The compound or a salt thereof according to claim 4, wherein $R^{12}$, $R^{14}$, $R^{15}$, and $R^{17}$ represent a hydrogen atom, $R^{13}$ and $R^{16}$ independently represent a halogen atom, $R^{18}$ and $R^{19}$ independently represent a phenyl group which may be substituted, and $R^{22}$ represents a hydrogen atom.

6. The compound or a salt thereof according to claim 4, wherein $R^{12}$, $R^{14}$, $R^{15}$, and $R^{17}$ represent a hydrogen atom, $R^{13}$ and $R^{16}$ represent a chlorine atom, $R^{18}$ and $R^{19}$ represent a phenyl group, and $R^{22}$ represents a hydrogen atom.

7. A composition for measurement of singlet oxygen, said composition comprising a compound or a salt thereof as recited in claim 1.

8. A method for measurement of singlet oxygen, which comprises:

(A) reacting a compound or a salt thereof with singlet oxygen, said compound represented by the following general formula (I):

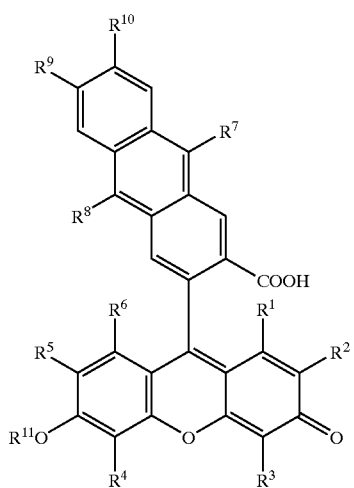

wherein $R^1$, $R^2$, $R^3$, $R^4$, $R^5$, and $R^6$ independently represent a hydrogen atom, a halogen atom, a $C_{1-6}$ alkyl group, or a $C_{1-6}$ alkoxyl group, $R^7$ and $R^8$ independently represent a $C_{1-6}$ alkyl group or an aryl group which may be substituted, $R^9$ and $R^{10}$ independently represent a hydrogen atom, a $C_{1-6}$ alkyl group, or a $C_{1-6}$ alkoxyl group, and $R^{11}$ represents a hydrogen atom or a $C_{1-12}$ alkanoyl group, or a salt thereof, and (B) measuring fluorescence of a compound or salt thereof produced in (A) having the general formula (II):

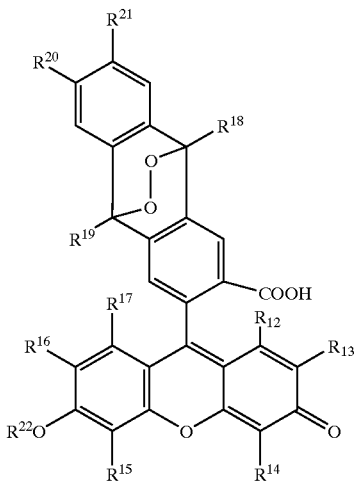

wherein $R^{12}$, $R^{13}$, $R^{14}$, $R^{15}$, $R^{16}$, and $R^{17}$ independently represent a hydrogen atom, a halogen atom, a $C_{1-6}$ alkyl group, or a $C_{1-6}$ alkoxyl group, $R^{18}$ and $R^{19}$ independently represent a $C_{1-6}$ alkyl group or an aryl group which may be substituted, $R^{20}$ and $R^{21}$ independently represent a hydrogen atom, a $C_{1-6}$ alkyl group, or a $C_{1-6}$ alkoxyl group, and $R^{22}$ represents a hydrogen atom or a $C_{1-12}$ alkanoyl group, or a salt thereof.

9. A compound represented by the following general formula (III):

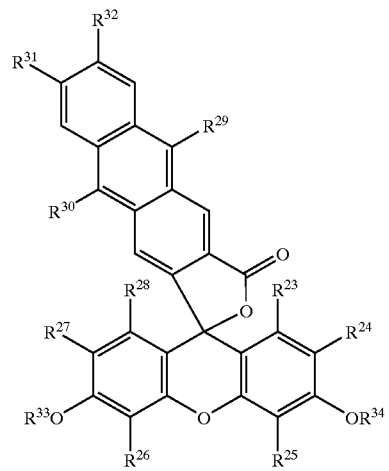

wherein $R^{23}$, $R^{24}$, $R^{25}$, $R^{26}$, $R^{27}$, and $R^{28}$ independently represent a hydrogen atom, a halogen atom, a $C_{1-6}$ alkyl group, or a $C_{1-6}$ alkoxyl group, $R^{29}$ and $R^{30}$ independently represent a $C_{1-6}$ alkyl group or an aryl group which may be substituted, $R^{31}$ and $R^{32}$ independently represent a hydrogen atom, a $C_{1-6}$ alkyl group, or a $C_{1-6}$ alkoxyl group, and $R^{33}$ and $R^{34}$ independently represent a $C_{1-12}$ alkanoyl group, or a salt thereof.

10. A composition for measurement of singlet oxygen, said composition comprising a compound or a salt thereof as recited in claim 9.

11. A compound represented by the following general formula (IV):

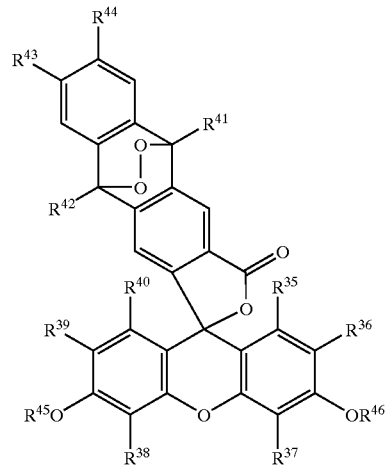

wherein $R^{35}$, $R^{36}$, $R^{37}$, $R^{38}$, $R^{39}$ and $R^{40}$ independently represent a hydrogen atom, a halogen atom, a $C_{1-6}$ alkyl group, or a $C_{1-6}$ alkoxyl group, $R^{41}$ and $R^{42}$ independently represent a $C_{1-6}$ alkyl group or an aryl group which may be substituted, $R^{43}$ and $R^{44}$ independently represent a hydrogen atom, a $C_{1-6}$ alkyl group, or a $C_{1-6}$ alkoxyl group, and $R^{45}$ and $R^{46}$ independently represents a $C_{1-12}$ alkanoyl group, or a salt thereof.

12. A composition for measurement of singlet oxygen, said composition comprising a compound or a salt thereof as recited in claim 2.

13. A composition for measurement of singlet oxygen, said composition comprising a compound or a salt thereof as recited in claim 3.

14. The method for measurement of singlet oxygen according to claim 8, wherein $R^1$, $R^3$, $R^4$, and $R^6$ represent a hydrogen atom, $R^2$ and $R^5$ independently represent a halogen atom, $R^7$ and $R^8$ independently represent a phenyl group which may be substituted, and $R^{11}$ represents a hydrogen atom.

15. The method for measurement of singlet oxygen according to claim 8, wherein $R^1$, $R^3$, $R^4$, and $R^6$ represent a hydrogen atom, $R^2$ and $R^5$ represent a chlorine atom, $R^7$ and $R^8$ represent a phenyl group, and $R^{11}$ represents a hydrogen atom.

16. The method for measurement of singlet oxygen according to claim 8, wherein $R^{12}$, $R^{14}$, $R^{15}$, and $R^{17}$ represent a hydrogen atom, $R^{13}$ and $R^{16}$ independently represent a halogen atom, $R^{18}$ and $R^{19}$ independently represent a phenyl group which may be substituted, and $R^{22}$ represents a hydrogen atom.

17. The method for measurement of singlet oxygen according to claim 8, wherein $R^{12}$, $R^{14}$, $R^{15}$, and $R_{17}$ represent a hydrogen atom, $R^{13}$ and $R^{16}$ represent a chlorine atom, $R^{18}$ and $R^{19}$ represent a phenyl group, and $R^{22}$ represents a hydrogen atom.

* * * * *